US006890521B2

(12) United States Patent  
Bonda

(10) Patent No.: US 6,890,521 B2
(45) Date of Patent: *May 10, 2005

(54) PHOTOSTABILIZATION OF A SUNSCREEN COMPOSITION WITH LOW LEVELS OF AN α-CYANO-β, β-DIPHENYLACRYLATE

(75) Inventor: Craig A. Bonda, Winfield, IL (US)

(73) Assignee: The C.P. Hall Company, Chicago, IL (US)

( * ) Notice: Subject to any disclaimer, the term of this patent is extended or adjusted under 35 U.S.C. 154(b) by 41 days.

This patent is subject to a terminal disclaimer.

(21) Appl. No.: 10/361,223

(22) Filed: Feb. 10, 2003

(65) Prior Publication Data

US 2004/0047818 A1 Mar. 11, 2004

Related U.S. Application Data

(63) Continuation-in-part of application No. 10/241,388, filed on Sep. 6, 2002, now abandoned.

(51) Int. Cl.$^7$ .............................. A61K 7/00; A61K 7/42; A61K 7/44
(52) U.S. Cl. ............................ 424/59; 424/60; 424/401
(58) Field of Search .............................. 424/401, 59, 60

(56) References Cited

U.S. PATENT DOCUMENTS

| | | | |
|---|---|---|---|
| 3,215,724 A | 11/1965 | Strobel et al. | |
| 3,215,725 A | 11/1965 | Strobel et al. | |
| 3,272,855 A | 9/1966 | Strobel et al. | |
| 3,275,520 A | 9/1966 | Strobel et al. | |
| 3,337,357 A | 8/1967 | Strobel et al. | |
| 3,445,545 A | 5/1969 | Skoultchi | |
| 3,992,356 A | 11/1976 | Jacquet et al. | |
| 4,107,290 A | 8/1978 | Jacquet et al. | |
| 4,387,089 A | 6/1983 | De Polo | |
| 4,489,057 A | 12/1984 | Welters et al. | |
| 4,562,067 A | 12/1985 | Hopp et al. | |
| 5,210,275 A | 5/1993 | Sabatelli | |
| 5,576,354 A | 11/1996 | Deflandre et al. | |
| 5,882,633 A | 3/1999 | Pisson et al. | |
| 5,972,324 A | 10/1999 | Zofchak et al. | |
| 5,993,789 A | 11/1999 | Bonda et al. | |
| 6,033,649 A | 3/2000 | Gonzenbach et al. | |
| 6,113,931 A | * 9/2000 | Bonda et al. | 424/401 |
| 6,126,925 A | * 10/2000 | Bonda et al. | 424/59 |
| 6,129,909 A | * 10/2000 | Bonda et al. | 424/70.1 |
| 6,180,091 B1 | * 1/2001 | Bonda et al. | 424/70.1 |
| 6,284,916 B1 | 9/2001 | Bonda et al. | |
| 6,444,195 B1 | * 9/2002 | Cole et al. | 424/60 |
| 6,485,713 B1 | 11/2002 | Bonda et al. | |
| 6,491,901 B2 | 12/2002 | Gers-Barlag et al. | |
| 6,555,095 B1 | * 4/2003 | Garrison | 424/59 |
| 2001/0022966 A1 | 9/2001 | Gers-Barlag et al. | |

FOREIGN PATENT DOCUMENTS

WO     WO 00/44340     8/2000

OTHER PUBLICATIONS

"Photostability of HallStar Photostable SPF 32 Sunscreen Compared to Neutrogena UVA/UVB Sunblock SPF 30," Suncare Research Laboratories, Memphis, Tennessee (Oct. 5, 2000).

Beckwith, in "The chemistry of amides: Synthesis of amides," Zabicky, J., Ed. Interscience: New York, pp. 73–185 (1970).

Bentley et al., "Medium Effects on the Rates and Mechanisms of Solvolytic Reactions," *Adv. Phys. Org. Chem.*, vol. 14, pp. 1–67 (1977).

Bentley et al., "$Y_x$ Scales of Solvent Ionizing Power," *Progr. Phys. Org. Chem.*, vol. 17, pp. 121–158 (1990).

Dimroth et al., *Justus Liebigs Ann. Chem.*, vol. 661 pp. 1–37 (1963).

Fainberg et al., "Correlation of Solvolysis Rates. III. t–Butyl Chloride in a Wide Range of Solvent Mextures," *J. Am. Chem. Soc.*, vol. 78 pp. 2770–2777 (1956).

Grunwald et al., "The Correlation of Solvolysis Rates," *J. Am. Chem. Soc.*, vol. 70, pp. 846–854 (1948).

Haslem, "Recent Developments in Methods for the Esterification and Protection of the Carboxyl Group," *Tetrahedron*, vol. 36, pp. 2409–2433 (1980).

Kamlet et al., "An Examination of Linear Solvation Energy Relationships," *Progr. Phys. Org. Chem.*, vol. 13, pp. 485–630 (1981).

Kosower, "The Effect of Solvent on Spectra . . . A New Empirical Measure of Solvent Polarity Z–Values," *J. Am. Chem. Soc.*, vol. 80, pp. 3253–3260 (1958).

McNaught et al., "IUPAC Compendium, of Chemical Terminology," 2nd Ed. (1997).

Reichardt, "Solvents and Solvent Effects in Organic Chemistry," 2nd Ed., Chap. 7: Empirical Parameters of Solvent Polarity, VCH Publishers, New York, New York (1998).

Sayre et al., "Photostability Testing of Avobenzone," Allured's Cosmetics & Toiletries Magazine, vol. 114, No. 5, pp. 85–91 (May 1999).

Tarras–Wahlberg et al., "Changes in Ultraviolet Absorption of Sunscreens After Ultraviolet Radiation," *J. Investigative Dermatology*, vol. 113, No. 4, pp. 547–553 (1999).

Turro, *Modern Molecular Photochemistry* Benjamin/Cummings Publ. Col. Menlo Park, California, pp. 296–361 (1991).

* cited by examiner

*Primary Examiner*—Gary Kunz
*Assistant Examiner*—Marina Lamm
(74) *Attorney, Agent, or Firm*—Marshall, Gerstein & Borun LLP

(57) ABSTRACT

Sunscreen compositions, including a mixture of a dibenzoylmethane derivative, and low and very low levels of an α-cyano-β,β-diphenylacrylate compound and, optionally, together with one or more diesters and polyesters of naphthalene dicarboxylic acid and a methoxy-substituted benzophenone.

14 Claims, 4 Drawing Sheets

PHOTOSTABILIZATION OF A SUNSCREEN COMPOSITION WITH LOW LEVELS OF AN α-CYANO-β, β-DIPHENYLACRYLATE

CROSS-REFERENCE TO RELATED APPLICATION

This application is a continuation-in-part of application Ser. No. 10/241,388 filed Sep. 6, 2002, now abandoned.

BACKGROUND OF THE INVENTION

1. Field of the Invention

The invention relates to sunscreen compositions including a dibenzoylmethane derivative that are made more stable by the addition of low levels of an α-cyano-β,β-diphenylacrylate compound. More particularly, the invention relates to sunscreen compositions which utilize low levels and very low levels of octocrylene to stabilize other photoactive compounds present in a sunscreen composition and, in particular, to stabilize dibenzoylmethane derivatives.

2. Brief Description of Related Technology

It is well known that ultraviolet radiation (light) having a wavelength from about 280 nm or 290 nm to about 320 nm (UV-B) is harmful to human skin, causing burns that are detrimental to the development of a good sun tan. UV-A radiation (about 320 nm to about 400 nm), while producing tanning of the skin, also can cause damage, particularly to very lightly-colored or sensitive skin, leading to reduction of skin elasticity and to wrinkles. Therefore, a sunscreen composition for use on human skin preferably includes both a UV-A and a UV-B filter to prevent most of the sunlight within the full range of about 280 nm or 290 nm to about 400 nm from damaging human skin.

Ultraviolet radiation from the sun or artificial sources can also cause harm to coatings containing photoactive substances, such as photoactive pigments and dyes, by breaking down chemical bonds in the structure of a component such as a polymer, a pigment, or a dye. This photodegradation can lead to color fading, loss of gloss, and loss of physical and protective properties of a coating. Photodegradation can take place in several steps which include one or more components of a coating absorbing UV radiation. The absorbed radiation can excite the absorbing molecules and raise them to a higher energy level, which can be very reactive. If the molecule cannot be relaxed, bond cleavage and the formation of free radicals will occur. These free radicals can attack one or more color molecules and/or a polymer backbone and form more free radicals. UV-A and UV-B filters can also be used to accept UV radiation to protect a pigmented coating.

The UV-B filters that are most widely used in the U.S. in commercial sunscreen compositions are paramethoxycinnamic acid esters, such as 2-ethylhexyl paramethoxycinnamate, commonly referred to as octyl methoxycinnamate or PARSOL MCX, octyl salicylate, and oxybenzone.

The organic UV-A filters most commonly used in commercial sunscreen compositions are the dibenzoylmethane derivatives, particularly 4-(1,1-dimethylethyl)-4'-methoxydibenzoylmethane (also called avobenzone, sold under the brand name PARSOL 1789). Other dibenzoylmethane derivatives described as UV-A filters are disclosed in U.S. Pat. Nos. 4,489,057, 4,387,089 and 4,562,067, the disclosures of which are hereby incorporated herein by reference. It is also well known that the above described UV-A filters, particularly the dibenzoylmethane derivatives, can suffer from rapid photochemical degradation, when used alone or when combined with the above-described most commercially used UV-B filters.

The performance of a photoactive compound or a combination of photoactive compounds in a sunscreen composition has been extremely difficult to predict based on the levels of photoactive compounds in the formulation, particularly when the formulation includes one or more photoactive compounds that suffer from relatively rapid photodegradation, such as avobenzone. Because of this, each formulation has required expensive laboratory testing to determine the UV absorbance, as a function of time (quantity) of exposure of the formulation to UV radiation. Moreover, a particularly difficult problem is presented when one photoactive compound in a sunscreen composition acts to increase the rate of photodegradation of another photoactive compound in the composition. This can be accomplished in a number or ways, including a bimolecular reaction between two photoactive compounds and a lowering of the threshold energy need to raise a photoactive compound to its excited state. For example, when avobenzone is combined with octyl methoxycinnamate a bimolecular pathway leads to the rapid photodegradation of both the dibenzoylmethane derivative and the octyl methoxycinnamate.

Methods and compositions for stabilizing photoactive compounds, such as dibenzoylmethane derivatives, with diesters and/or polyesters of naphthalene dicarboxylic acid are described in U.S. Pat. Nos. 5,993,789, 6,284,916 and Gers-Barlag, et al. U.S. Pat. No. 6,491,901 ('901). Alternatively, Deflandre et al, U.S. Pat. No. 5,576,354 and Gonzenbach et al., U.S. Pat. No. 6,033,649 describe the use of high levels of an α-cyano-β,β-diphenylacrylate compound to stabilize a sunscreen composition including a dibenzoylmethane derivative. Thus, Deflandre et al. teach a minimum 1% by weight of octocrylene and Gonzenbach et al. teach a minimum of 0.5% by weight of octocrylene to stabilize a dibenzoylmethane derivative in a sunscreen composition. Gers-Barlag, et al. U.S. Pat. No. 6,491,901 ('901) discloses sunscreen compositions containing a dibenzoylmethane derivative with a stabilizing combination of octocrylene and diesters or polyesters of naphthalene dicarboxylic acid wherein the examples have a weight ratio of octocrylene to the diester or polyester of naphthalene dicarboxylic acid in the range of 0.16 to 0.725.

SUMMARY

One aspect of the invention is a composition including a mixture of a dibenzoylmethane derivative, less than about 1% by weight of the total weight of the composition of (a) an α-cyano-β,β-diphenylacrylate compound, and (b) a diester or polyester of naphthalene dicarboxylic acid.

Another aspect of the invention is a composition including a mixture of a dibenzoylmethane derivative, less than about 1% by weight of the total weight of the composition of (a) an α-cyano-β,β-diphenylacrylate compound, and (b) a diester or polyester of naphthalene dicarboxylic acid, wherein the weight ratio of (a) to (b) is 0.1 or less, preferably 0.05 or less.

Another aspect of the invention is a composition including a mixture of a dibenzoylmethane derivative and less than 0.5% by weight of the total weight of the composition of an α-cyano-β,β-diphenylacrylate compound.

Another aspect of the invention is a composition including a mixture of (a) a dibenzoylmethane derivative, (b) less than 0.5% by weight of the total weight of the composition of an α-cyano-β,β-diphenylacrylate compound, and (c) a diester or polyester of naphthalene dicarboxylic acid, wherein the weight ratio of (b) to (c) is 0.1 or less, preferably 0.05 or less, more preferably 0.027 or less, most preferably 0.01 to 0.026.

Yet another aspect of the invention is a composition including a mixture of a dibenzoylmethane derivative, an α-cyano-β,β-diphenylacrylate compound, and a diester or polyester of naphthalene dicarboxylic acid, wherein the sunscreen composition has an oil phase that has a high polarity, for example an oil phase that has a high polarity may have a dielectric constant of at least about 7, preferably at least about 8.

DETAILED DESCRIPTION OF THE PREFERRED EMBODIMENTS

Figure 1:
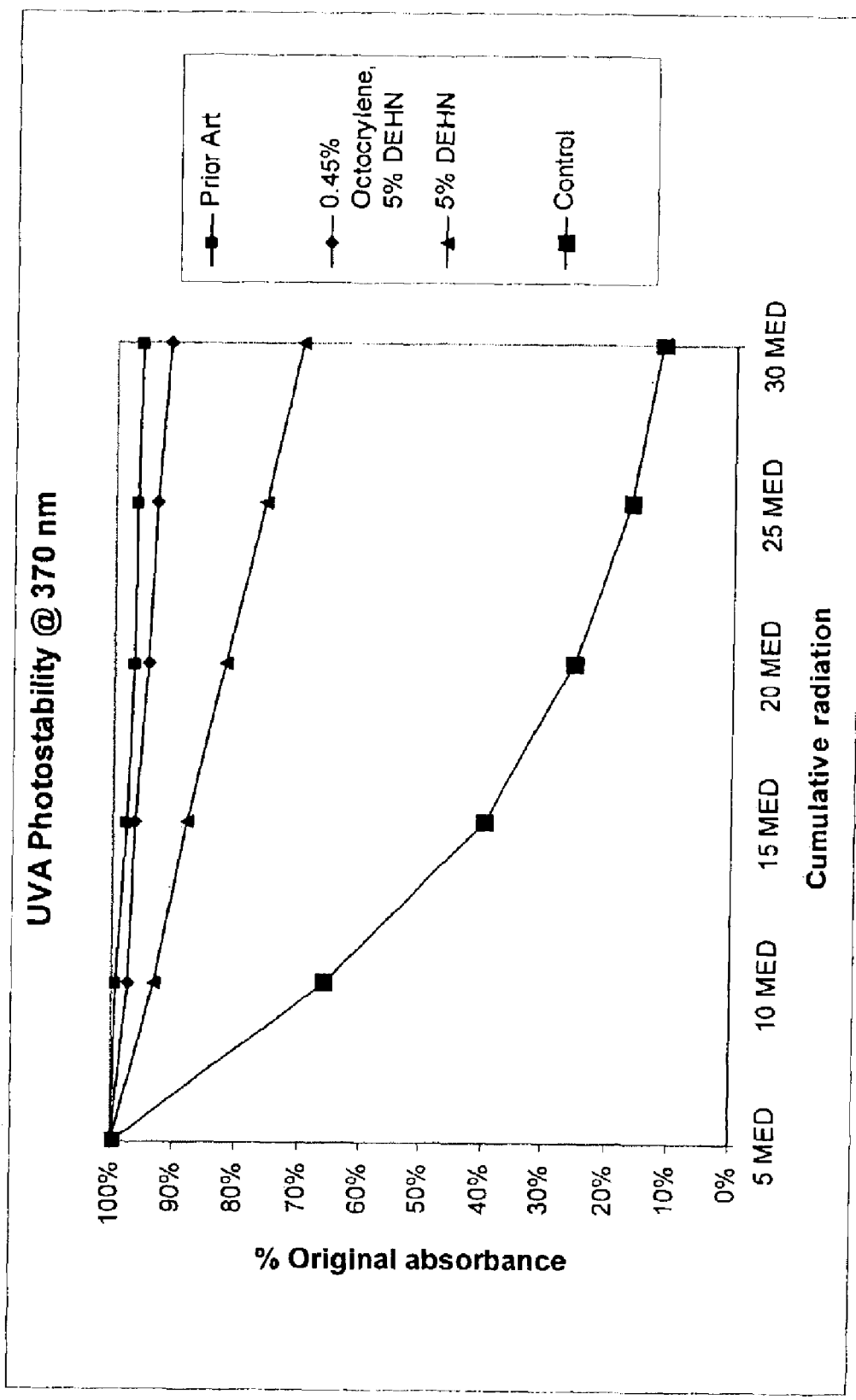
FIG. 1 is a graph of the percent absorbance of the sunscreen compositions listed in Table II at various intervals of exposure to radiation in minimal erythermal dose (MED) units, wherein 1 MED is 21 millijoules per square centimeter (mJ/cm$^2$).

Sunscreen compositions containing a dibenzoylmethane derivative UV-A filter compound, such as 4-(1,1-dimethylethyl)-4'-methoxydibenzoylmethane (PARSOL® 1789), and low levels (e.g., less than 0.5% by weight) and very low levels (e.g., less than 0.3% by weight) of an α-cyano-β,β-diphenylacrylate compound to increase the photostability of the dibenzoylmethane derivative are described herein. One aspect of the sunscreen compositions disclosed herein involves the use of low levels (e.g., less than 0.5% by weight) and very low levels (e.g., less than 0.21% by weight) of (a) an α-cyano-β,β-diphenylacrylate compound, and (b) a diester or polyester of naphthalene dicarboxylic acid (DEHN), wherein the weight ratio of (a) to (b) is 0.01 to less than 0.10, preferably less than or equal to 0.027, more preferably in the range of 0.01 to 0.026, to achieve a stable sunscreen composition. Another aspect of the sunscreen compositions disclosed herein involves the use of an α-cyano-β,β-diphenylacrylate compound and a highly polar solvent or blend of solvents with a high polarity to achieve a stable sunscreen composition.

A photoactive compound can be considered stable when, for example, after 30 MED irradiation the photoactive compound has retained at least 90% of its original absorbance at a wavelength or a range of wavelengths of interest (e.g., the wavelength at which or near a photoactive compound has a peak absorbance, such as 350–370 nm for avobenzone). Likewise, a sunscreen composition can include a plurality of photoactive compounds and a sunscreen composition, as a whole, can be considered stable when, for example, after 30 MED irradiation the sunscreen composition has retained at least 90% of its original absorbance at one or more wavelengths of interest (e.g., at or near the peak absorbance wavelength of the primary photoactive compounds).

It has surprisingly been found that the addition of a low level of an α-cyano-β,β-diphenylacrylate compound to a sunscreen composition including a diester or polyester of naphthalene dicarboxylic acid significantly increases the photostability of the sunscreen composition. Without intending to be limited to any particular mechanism of achieving this increase in stability, it is believed that a diester or polyester of naphthalene dicarboxylic acid stabilizes a dibenzoylmethane derivative by accepting the triplet energy of the dibenzoylmethane derivative once the dibenzoylmethane derivative has reached an excited state as a result of the absorption of ultra-violet light. Once a dibenzoylmethane derivative is excited, it is prone to degrade according to a number of pathways, however, the degradation of the dibenzoylmethane derivative can be substantially reduced or prevented by the use of a diester or polyester of naphthalene dicarboxylic acid to quench (accept) the triplet excited state energy present in an excited dibenzoylmethane molecule. Thus, in one pathway of degradation, a dibenzoylmethane derivative is excited to its triplet state and the excited state triplet energy is released in a bond breaking step, thereby preventing the dibenzoylmethane derivative from further accepting ultra-violet radiation. A diester or polyester of naphthalene dicarboxylic acid may stabilize a dibenzoylmethane derivative by accepting the triplet state (excited state) energy of the excited dibenzoylmethane derivative in such a way as to convert the excited dibenzoylmethane derivative back to a non-excited state that is capable of re-accepting ultra-violet radiation (energy transfer).

For this process to work continuously, the diester or polyester of naphthalene dicarboxylic acid must transfer or convert the energy that was accepted from the excited dibenzoylmethane derivative. Without intending to be limited to a particular mechanism, it is believed that when a diester or polyester of naphthalene dicarboxylic acid is excited to its triplet state they dissipate the triplet excited state energy through vibrations (i.e., heat), which in this group of molecules is a slow mode of dissipating energy. It has been found, quite surprisingly, that by the addition of low levels (e.g., less than 1% by weight) or very low levels (e.g., 0.5% by weight or less) of an α-cyano-β,β-diphenylacrylate compound, the α-cyano-β,β-diphenylacrylate compound is able to accept triplet excited state energy in an excited diester or polyester of naphthalene dicarboxylic acid. Thus, according to one possible mechanism, the efficiency of the dissipation of the excited state energy in an excited diester or polyester of naphthalene dicarboxylic acid is greatly improved by a transfer of energy from an excited diester or polyester of naphthalene dicarboxylic acid to an α-cyano-β,β-diphenylacrylate compound.

Without intending to be limited to any particular mechanism by which an α-cyano-β,β-diphenylacrylate compound is able to quench the excited state of a diester or polyester of naphthalene dicarboxylic acid, it is believed that the α-cyano-β,β-diphenylacrylate compound accepts the excited state energy and dissipates the energy kinetically in the form of rapid isomerizations. This process is shown below:

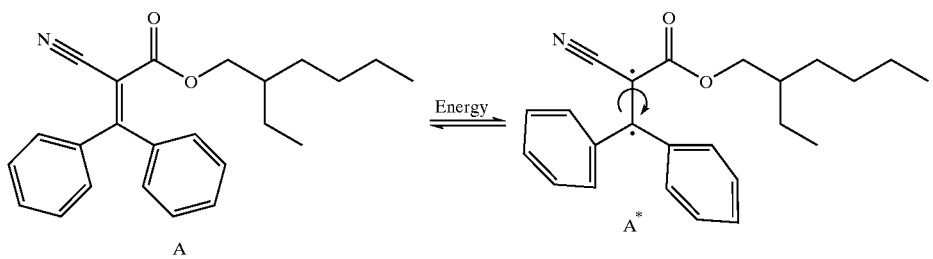

wherein the α-cyano-β,β-diphenylacrylate compound (octocrylene shown above as A), accepts the triplet excited state energy and forms a diradical (shown above as A*) at the α and β positions of the acrylate, which converts the double bond into a single bond and allows for the free rotation of the phenyl groups. This rotation occurs rapidly and efficiently to dissipate any excited state energy accepted by the α-cyano-β,β-diphenylacrylate compound. In solution (e.g., a sunscreen composition), a key limitation on one compound's ability to stabilize another is the ability of the two compounds to come into contact with one another. Thus, according to this mechanism of stabilization, it is preferred to have an excess of a diester and polyester of naphthalene dicarboxylic acid as compared to the α-cyano-β,β-diphenylacrylate compound so that the α-cyano-β,β-diphenylacrylate compound can quickly come into contact with an excited diester or polyester of naphthalene dicarboxylic acid. Moreover, the weight ratio of the diester and polyester of naphthalene dicarboxylic acid to the α-cyano-β,β-diphenylacrylate compound is, preferably, at least about 6:1.

Commonly-assigned U.S. Pat. No. 6,485,713 and application Ser. No. 10/092,131, the disclosures of which are hereby incorporated herein by reference, describe compositions and methods for increasing the stability of photoactive compounds in a sunscreen composition, e.g., by the addition of polar solvents to the oil phase of a composition. It has been found, quite surprisingly, that by increasing the polarity of the oil phase of a sunscreen composition including low levels and very low levels of an α-cyano-β,β-diphenylacrylate compound, the stability of the sunscreen composition is increased. Now knowing that the polarity of the solution affects the stability, one might expect that the more polar the solution is, the greater the stability it will impart to the photoactive compound. In contrast, and even more surprisingly, it has been found that as the polarity of a solvent system including a dissolved, rapidly-photodegradable compound is increased, the rate of photodecay initially decreases—but then increases again as the polarity is further increased. Thus, a photodegradable compound in solution will degrade as a second-order function of the overall polarity of the solution. Currently accepted photochemical theory provides the possibility that the mechanism by which a photodegradable compound is stabilized is the transfer of a photonically-excited electron to a nearby molecule of the same or different species (see, e.g., N. J. Turro, Modern Molecular Photochemistry, Chapter 9, Benjamin/Cummings Publ. Co., Menlo Park, Calif. (1991)), however photochemical theory does not describe the observed phenomena. Though not intending to be bound by such a belief, the observed phenomena are believed to coincide with the electron transfer theory of Professor Rudolph A. Marcus of the California Institute of Technology, for which he received the 1992 Nobel Prize in Chemistry.

The dielectric constant of a solvent system is a preferred measure of polarity of a solvent system, for example because the dielectric constant is a measure of both inherent and inducible dipole moments. Other measures of polarity include, but are not limited to, the induced and/or inherent (permanent) dipole moment (e.g., in Debye units), the Dimroth-Reichardt $E_T$ parameter, and ionizing power. See generally, C. Reichardt, "Solvents and Solvent Effects in Organic Chemistry" 2nd ed., Chap. 7: Empirical Parameters of Solvent Polarity, VCH Publishers, New York, N.Y., (1988). Moreover, a more detailed description of these methods of measuring the polarity of the compound or a series of compounds can be found in commonly assigned U.S. patent application Ser. Nos. 10/092,131 and 10/092,132.

Mathematically, photodegradation can be described by an exponential function. Thus, Q(a), the absorbance after a radiation dose (i.e., exposure to a quantity of radiation), can be described by the general equation (i), $$Q(a)=Ae^{-kr} \qquad (i)$$

wherein A is the original (pre-exposure) absorbance, e is the natural logarithm base, k is the rate constant of the photodecay, and r is the cumulative dose (e.g., in MED units). Because the absorbance decreases as the cumulative dose increases (photodecay), the overall term −k will be negative, and the greater the value of −k (i.e., closer to zero) and, thus, the lower the rate constant of photodecay, the lower is the rate of photodecay. For example, when Q(a) is plotted on a log scale versus r on a linear scale, the function forms a straight line with a slope equal to −k.

Furthermore, it has been found that, for a set of photoactive compounds that includes a photodegradable compound (e.g. avobenzone), the rate constant of photodecay of the set of photoactive compounds can be described as a second-order function of the polarity, preferably the dielectric constant (i.e., relative permittivity) of the filter set dissolved in the solvent system. Thus, for example, the rate constant of photodecay of a filter set that include one or more of a photoactive compound, can be described by the general equation (ii), $$k=-(x\epsilon^2+y\epsilon+z) \qquad (ii)$$

wherein x, y, and z can be empirically determined. The dielectric constant at the theoretical minimum rate constant of photodecay −k min described by formula (iii), $$\varepsilon_{k\,min} = \frac{-y}{2x} \qquad (iii)$$

wherein x and y are defined as above.

The phenomena described above, coupled with the knowledge that, heretofore, sunscreen compositions have been formulated without specific regard to the relationship between polarity and photostability and, in newly-discovered fact, have had non-optimal polarities, forms the basis for at least one aspect of the compositions described herein.

A photoactive compound is one that responds to light photoelectrically. In the compositions disclosed herein, a photoactive compound is one that responds to UV radiation photoelectrically. For example, photoactive compounds that respond to UV radiation photoelectrically by rapid photo degradation can benefit highly from the compositions disclosed herein, even though the benefits of the compositions disclosed herein are not limited to such compounds. Photostability is a potential problem with all UV filters because they are deliberately selected as UV-absorbing molecules. In other applications, a photoactive compound may be a pigment or a dye (e.g., a hydrophobic dye).

UV filters include compounds selected from the following categories (with specific examples) including: p-aminobenzoic acid, its salts and its derivatives (ethyl, isobutyl, glyceryl esters; p-dimethylaminobenzoic acid); anthranilates (o-aminobenzoates; methyl, menthyl, phenyl, benzyl, phenylethyl, linalyl, terpinyl, and cyclohexenyl esters); salicylates (octyl, amyl, phenyl, benzyl, menthyl (homosalate), glyceryl, and dipropyleneglycol esters); cinnamic acid derivatives (menthyl and benzyl esters, alpha-phenyl cinnamonitrile; butyl cinnamoyl pyruvate); dihydroxycinnamic acid derivatives (umbelliferone, methylumbelliferone, methylaceto-umbelliferone); camphor derivatives (3-benzylidene, 4-methylbenzylidene, polyacrylamidomethyl benzylidene, benzalkonium methosulfate, benzylidene camphor sulfonic acid, and terephthalylidene dicamphor sulfonic acid); trihydroxycinnamic acid derivatives (esculetin, methylesculetin, daphnetin, and the glucosides, esculin and daphnin); hydrocarbons (diphenylbutadiene, stilbene); dibenzalacetone; benzalacetophenone; naphtholsulfonates (sodium salts of 2-naphthol-3,6-disulfonic and of 2-naphthol-6,8-disulfonic acids); dihydroxy-naphthoic acid and its salts; o- and p-hydroxydiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric acid derivatives; vilouric acid derivatives; tannic acid and its derivatives; hydroquinone; and benzophenones (oxybenzone, sulisobenzone, dioxybenzone, benzoresorcinol, 2,2',4,4'-tetrahydroxybenzophenone, 2,2'-dihydroxy-4,4'-dimethoxybenzophenone, octabenzone, 4-isopropyldibenzoylmethane, butylmethoxydibenzoylmethane, etocrylene, and 4-isopropyl-dibenzoylmethane).

Particularly useful are: 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl 4-[bis(hydroxypropyl)] aminobenzoate, 2-ethylhexyl-2-cyano-3,3-diphenylacrylate, 2-ethylhexylsalicylate, glycerol p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl-5-sulfoniobenzoxazoic acid, and combinations thereof.

A sunscreen composition disclosed herein includes a dibenzoylmethane derivative. Preferred dibenzoylmethane derivatives include 2-methyldibenzoylmethane; 4-methyldibenzoylmethane; 4-isopropyldibenzoylmethane; 4-tert-butyldibenzoylmethane; 2,4-dimethyldibenzoylmethane; 2,5-dimethyldibenzoylmethane; 4,4'-diisopropyldibenzoylmethane; 4,4'-dimethoxydibenzoylmethane; 4-tert-butyl-4'-methoxydibenzoylmethane; 2-methyl-5-isopropyl-4'-methoxydibenzoylmethane; 2-methyl-5-tert-butyl-4'-methoxydibenzoylmethane; 2,4-dimethyl-4'-methoxydibenzoylmethane; 2,6-dimethyl-4-tert-butyl-4'-methoxydibenzoylmethane, and combinations thereof. The compositions disclosed herein preferably include a dibenzoylmethane derivative in a range of about 0.1% to about 25% by weight of the total weight of the composition.

In any embodiment of a sunscreen composition an additional photoactive compound can be added to the composition. Additional photoactive compounds can be selected from any of the UV-A filters, UV-B filters, and combinations thereof. In a cosmetically-acceptable sunscreen embodiment for use on human skin, a photoactive compound preferably is selected from approved (if regulated), cosmetically-acceptable UV-A filters, UV-B filters, and combinations thereof.

For example, for a product marketed in the United States, preferred cosmetically-acceptable photoactive compounds and concentrations (reported as a percentage by weight of the total cosmetic sunscreen composition) include: aminobenzoic acid (also called para-aminobenzoic acid and PABA; 15% or less), avobenzone (also called butyl methoxy dibenzoylmethane; 3% or less), cinoxate (also called 2-ethoxyethyl p-methoxycinnamate; 3% or less), dioxybenzone (also called benzophenone-8; 3% or less), homosalate (15% or less), menthyl anthranilate (also called menthyl 2-aminobenzoate; 5% or less), octocrylene (also called 2-ethylhexyl-2-cyano-3,3 diphenylacrylate; 10% or less), octyl methoxycinnamate (7.5% or less), octyl salicylate (also called 2-ethylhexyl salicylate; 5% or less), oxybenzone (also called benzophenone-3; 6% or less), padimate O (also called octyl dimethyl PABA; 8% or less), phenylbenzimidazole sulfonic acid (water soluble; 4% or less), sulisobenzone (also called benzophenone-4; 10% or less), titanium dioxide (25% or less), trolamine salicylate (also called triethanolamine salicylate; 12% or less), and zinc oxide (25% or less).

Other preferred cosmetically-acceptable photoactive compounds and concentrations (percent by weight of the total cosmetic sunscreen composition) include diethanolamine methoxycinnamate (10% or less), ethyl-[bis (hydroxypropyl)]aminobenzoate (5% or less), glyceryl aminobenzoate (3% or less), 4-isopropyl dibenzoylmethane (5% or less), 4-methylbenzylidene camphor (6% or less), terephthalylidene dicamphor sulfonic acid (10% or less), and sulisobenzone (also called benzophenone-4, 10% or less).

For a product marketed in the European Union, preferred cosmetically-acceptable photoactive compounds and concentrations (reported as a percentage by weight of the total cosmetic sunscreen composition) include: PABA (5% or less), camphor benzalkonium methosulfate (6% or less), homosalate (10% or less), benzophenone-3 (10% or less), phenylbenzimidazole sulfonic acid (8% or less, expressed as acid), terephthalidene dicamphor sulfonic acid (10% or less, expressed as acid), butyl methoxydibenzoylmethane (5% or less), benzylidene camphor sulfonic acid (6% or less, expressed as acid), octocrylene (10% or less, expressed as acid), polyacrylamidomethyl benzylidene camphor (6% or less), ethylhexyl methoxycinnamate (10% or less), PEG-25 PABA (10% or less), isoamyl p-methoxycinnamate (10% or less), ethylhexyl triazone (5% or less), drometrizole trielloxane (15% or less), diethylhexyl butamido triazone (10% or less), 4-methylbenzylidene camphor (4% or less), 3-benzylidene camphor (2% or less), ethylhexyl salicylate (5% or less), ethylhexyl dimethyl PABA (8% or less), benzophenone-4 (5%, expressed as acid), methylene bis-benztriazolyl tetramethylbutylphenol (10% or less), disodium phenyl dibenzimidazole tetrasulfonate (10% or less, expressed as acid), bis-ethylhexyloxyphenol methoxyphenol triazine (10% or less), methylene bisbenzotriazolyl tetramethylbutylphenol (10% or less, also called TINOSORB M), and bisethylhexyloxyphenol methoxyphenyl triazine.(10% or less, also called TINOSORB S).

All of the above-described UV filters are commercially available. For example, suitable commercially-available organic UV filters are identified by trade name and supplier in Table 1 below:

A sunscreen composition disclosed herein may include a variety of photoactive compounds, including one or more UV-A photoactive compounds and one or more UV-B photoactive compounds. Preferably, a sunscreen composition includes a photoactive compound selected from the group consisting of p-aminobenzoic acid and salts and derivatives thereof; anthranilate and derivatives thereof; dibenzoylmethane and derivatives thereof; salicylate and derivatives thereof; cinnamic acid and derivatives thereof; dihydroxycinnamic acid and derivatives thereof; camphor and salts and derivatives thereof; trihydroxycinnamic acid and derivatives thereof; dibenzalacetone naphtholsulfonate and salts and derivatives thereof; benzalacetophenone naphtholsulfonate and salts and derivatives thereof; dihydroxynaphthoic acid and salts thereof; o-hydroxydiphenyldisulfonate and salts and derivatives thereof; p-hydroxydiphenyldisulfonate and salts and derivatives thereof; coumarin and derivatives thereof; diazole derivatives; quinine derivatives and salts thereof; quinoline derivatives; hydroxy-substituted benzophenone derivatives;

TABLE I

| CTFA Name | Trade Name | Supplier |
|---|---|---|
| benzophenone-3 | UVINUL M-40 | BASF Chemical Co. |
| benzophenone-4 | UVINUL MS-40 | BASF Chemical Co. |
| benzophenone-8 | SPECTRA-SORB UV-24 | American Cyanamid |
| DEA-methoxycinnamate | BERNEL HYDRO | Bernel Chemical |
| ethyl dihydroxypropyl-PABA | AMERSCREEN P | Amerchol Corp. |
| glyceryl PABA | NIPA G.M.P.A. | Nipa Labs. |
| homosalate | KEMESTER HMS | Humko Chemical |
| menthyl anthranilate | SUNAROME UVA | Felton Worldwide |
| octocrylene | UVINUL N-539 | BASF Chemical Co. |
| octyl dimethyl PABA | AMERSCOL | Amerchol Corp. |
| octyl methoxycinnamate | PARSOL MCX | Bernel Chemical |
| PABA | PABA | National Starch |
| 2-phenylbenzimidazole-5-sulphonic acid | EUSOLEX 6300 | EM Industries |
| TEA salicylate | SUNAROME W | Felton Worldwide |
| 2-(4-methylbenzildene)-camphor | EUSOLEX 6300 | EM Industries |
| benzophenone-1 | UVINUL 400 | BASF Chemical Co. |
| benzophenone-2 | UVINUL D-50 | BASF Chemical Co. |
| benzophenone-6 | UVINUL D-49 | BASF Chemical Co. |
| benzophenone-12 | UVINUL 408 | BASF Chemical Co. |
| 4-isopropyl dibenzoyl methane | EUSOLEX 8020 | EM Industries |
| butyl methoxy dibenzoyl methane | PARSOL 1789 | Givaudan Corp. |
| etocrylene | UVINUL N-35 | BASF Chemical Co. |
| methylene bisbenzotriazolyl tetramethylbutylphenol | TINOSORB M | Ciba Specialty Chemicals |
| bisethylhexyloxyphenol methoxyphenyl triazine. | TINOSORB S | Ciba Specialty Chemicals |

As used herein, the term "alkyl" includes straight chained and branched hydrocarbon groups containing the indicated number of carbon atoms, typically methyl, ethyl, propyl, and butyl groups. The term "alkyl" also includes "bridged alkyl," e.g., a $C_4$–$C_{16}$ bicyclic or polycyclic hydrocarbon group, for example, norbornyl, adamantyl, bicyclo[2.2.2]octyl, bicyclo[2.2.1]heptyl, bicyclo[3.2.1]octyl, or decahydronaphthyl. The term "cycloalkyl" is defined as a cyclic hydrocarbon group, e.g., cyclopropyl, cyclobutyl, cyclohexyl, and cyclopentyl.

As used herein, the term "alkenyl" is defined identically as "alkyl," except for containing a carbon-carbon double bond. The term "cycloalkenyl" is identical to "cycloalkyl" except containing a carbon-carbon double bond, e.g., cyclopropyl, cyclobutyl, cyclohexyl, and cyclopentyl.

As used herein, the term "aryl," alone or in combination, is defined herein as a monocyclic or polycyclic aromatic group, preferably a monocyclic or bicyclic aromatic group, e.g., phenyl or naphthyl.

methoxy-substituted benzophenone derivatives; uric acid derivatives; vilouric acid derivatives; tannic acid and derivatives thereof; hydroquinone; benzophenone derivatives; 1,3,5-triazine derivatives, phenyldibenzimidazole tetrasulfonate and salts and derivatives thereof; terephthalylidene dicamphor sulfonic acid and salts and derivatives thereof; methylene bis-benzotriazolyl tetramethylbutylphenol and salts and derivatives thereof; bis-ethylhexyloxyphenol methoxyphenyl triazine and salts and derivatives thereof; diethylamino hydroxybenzoyl hexyl benzoate and salts and derivatives thereof; and combinations of the foregoing.

A preferred combination of photoactive compounds in a sunscreen composition includes a UV-A and a UV-B photoactive compound. However, when 2-ethylhexyl-p-methoxycinnamate is included in a mixture with a dibenzoylmethane derivative, the dibenzoylmethane derivative becomes particularly unstable. Without intending to be limited to any particular mechanism, it is believed that the cinnamate ester reacts with an excited-state dibenzoylmethane derivative in a bimolecular pathway that renders both the dibenzoylmethane derivative and the cinnamate ester incapable of absorbing UV radiation. It has been found, quite surprisingly, that the use of low levels (e.g., less than 1% by weight) and very low levels (e.g., less than 0.5% by weight) of an α-cyano-β,β-diphenylacrylate compound increases the stability of a sunscreen composition including 2-ethylhexyl-p-methoxycinnamate and a dibenzoylmethane derivative. Thus, one embodiment of a sunscreen composition includes the photoactive compound 2-ethylhexyl-p-methoxycinnamate, a dibenzoylmethane derivative, and low levels or very low levels of an α-cyano-β,β-diphenylacrylate compound.

It has been found, quite surprisingly, that the addition of a methoxy-substituted benzophenone derivative to a sunscreen composition including a dibenzoylmethane derivative and a diester or polyester of naphthalene dicarboxylic acid results in an increase in the stability of the dibenzoylmethane derivative present in the composition. A methoxy-substituted benzophenone derivative has dual purposes in the sunscreen composition, both to act as a photoactive compound, and to increase the photostability (lower the rate constant of photodecay) of one or more photoactive compounds present in the sunscreen composition. Without intending to be limited to any particular mechanism, it is believed that a methoxy-substituted benzophenone derivative quenches (accepts) the singlet excited state of the diester or polyester of naphthalene dicarboxylic acid, and thereby prevents the excited diester or polyester from reaching the triplet excited state. Preferably, a sunscreen composition disclosed herein includes a methoxy-substituted benzophenone derivative such as benzophenone-3. The methoxy-substituted benzophenone derivative preferably is present in a sunscreen composition in an amount of 0.5% or less by weight of the total weight of the composition.

One embodiment of a sunscreen composition disclosed herein includes a mixture of a dibenzoylmethane derivative, less than 1% by weight of the total weight of the composition of an α-cyano-β,β-diphenylacrylate compound, and a diester or polyester of naphthalene dicarboxylic acid selected from the group consisting of formula (I), formula (II), and combinations thereof:

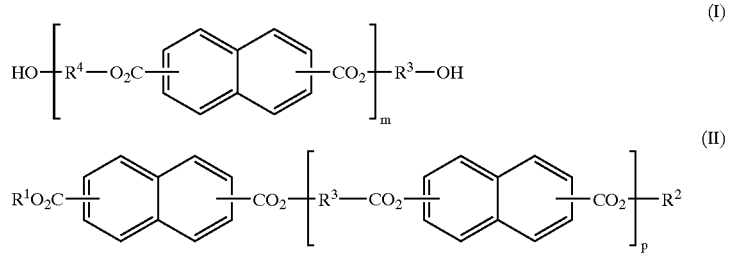

wherein $R^1$ and $R^2$ are the same or different and selected from the group consisting of $C_1$–$C_{22}$ alkyl groups, diols having the structure HO—$R^3$—OH, and polyglycols having the structure HO—$R^4$—(—O—$R^3$—)$_n$—OH; wherein each $R^3$ and $R^4$ is the same or different and selected from the group consisting of $C_1$–$C_6$ straight or branched chain alkyl groups; and wherein m and n are each in a range of 1 to 100 and p is in a range of 0 to 100. Although any α-cyano-β,β-diphenylacrylate compound may be used in this embodiment, preferably, the α-cyano-β,β-diphenylacrylate compound is 2-ethylhexyl-2-cyano-3,3-diphenylacrylate (also known as octocrylene). In some embodiments, the α-cyano-β,β-diphenylacrylate compound is present in the composition in an amount at least about 0.1% by weight of the total weight of the composition and less than 0.5% by weight of the total weight of the composition. In other embodiments have the α-cyano-β,β-diphenylacrylate compound is present in the composition in a range of 0.5% to 1% by weight of the total weight of the composition.

The method of preparation of particularly useful diesters and polyesters of naphthalene dicarboxylic acid and the use of diesters and polyesters of naphthalene dicarboxylic acid in a sunscreen composition are described in U.S. Pat. Nos. 5,993,789 and 6,284,916, the disclosures of which are hereby incorporated herein by reference. Preferably, a composition of this embodiment includes a diester of formula (II) wherein $R^1$ and $R^2$ are 2-ethylhexane and p is 0. Preferably, the compositions disclosed herein include a diester or polyester of naphthalene dicarboxylic acid in a range of about 0.1% to about 15% by weight of the total weight of the composition.

As described above, the stability of photoactive compounds present in a sunscreen composition can be increased by controlling the polarity of the oil phase of the composition. Because prior sunscreen formulations have typically had lower than optimal polarities, adding a high-polarity component to the oil phase to raise the oil phase polarity improves the photostability of the photoactive compounds. Thus, preferably, a sunscreen composition includes an oil phase comprising a dibenzoylmethane derivative and an α-cyano-β,β-diphenylacrylate compound, and a solvent system, wherein the solvent system includes an effective amount of a polar solvent, or a blend solvents with a high polarity, to increase the photostability of the dibenzoylmethane derivative or other photoactive compounds present in the sunscreen composition. Suitable polar solvents for use in a sunscreen composition are disclosed in commonly assigned U.S. patent application Ser. Nos. 10/097,131 and 10/092,132, the disclosures of which are hereby incorporated herein by reference. A composition of this embodiment preferably has a dielectric constant of at least about 8.

Another embodiment of the sunscreen compositions disclosed herein includes a mixture of a dibenzoylmethane derivative and less than 0.5% by weight of the total weight of the composition of an α-cyano-β,β-diphenylacrylate compound. Although any α-cyano-β,β-diphenylacrylate compound may be used according to this embodiment, preferably, the α-cyano-β,β-diphenylacrylate compound is 2-ethylhexyl-2-cyano-3,3-diphenylacrylate (also known as octocrylene). It is preferred that the α-cyano-β,β-diphenylacrylate compound is present in the composition in an amount at least about 0.1% by weight of the total weight of the composition. Preferably, the composition can include a diester or polyester of naphthalene dicarboxylic acid selected from the group consisting of formula (I), formula (II), and combinations thereof:

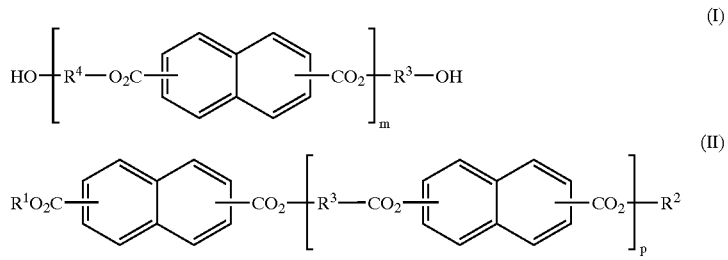

wherein R¹ and R² are the same or different and selected from the group consisting of $C_1$–$C_{22}$ alkyl groups, diols having the structure HO—$R^3$—OH, and polyglycols having the structure HO—$R^4$—(—O—$R^3$—)$_n$—OH; wherein each $R^3$ and $R^4$ are the same or different and selected from the group consisting of $C_1$–$C_6$ straight or branched chain alkyl groups; and wherein m and n are each in a range of 1 to 100 and p is in a range of 0 to 100. Preferably, a composition of this embodiment include a diester of formula (II) wherein $R^1$ and $R^2$ are 2-ethylhexane and p is 0. The compositions disclosed herein preferably include a diester or polyester of naphthalene dicarboxylic acid in a range of about 0.1% to about 15% by weight of the total weight of the composition. Preferably, the weight ratio of the α-cyano-β,β-diphenylacrylate compound to the diester or polyester of naphthalene dicarboxylic acid is 0.10 or less, more preferably in the range of about 0.01 to 0.027 or less, more preferably in the range of 0.01 to 0.26.

Another embodiment of a sunscreen composition disclosed herein includes a mixture of a dibenzoylmethane derivative and an α-cyano-β,β-diphenylacrylate compound, wherein said sunscreen composition has a dielectric constant of at least about 8.

EXAMPLES

The following examples are provided to illustrate the invention but are not intended to limit the scope of the invention.

Example 1

A series of sunscreen compositions was produced by mixing the ingredients and concentrations (formulations) shown in Table II below:

TABLE II

| Ingredients | Prior Art | 0.45% Octocrylene | 5% DEHN | Control |
|---|---|---|---|---|
| Oil Phase | | | | |
| Avobenzone | 2.00% | 2.00% | 2.00% | 2.00% |
| Octyl salicylate | 5.00% | 5.00% | 5.00% | 5.00% |
| Diethylhexyl 2,6-naphthalate | 0.00% | 5.00% | 5.00% | 0.00% |
| Octocrylene | 4.00% | 0.45% | 0.00% | 0.00% |
| $C_{12}$–$C_{15}$ alkyl benzoates | 10.00% | 0.00% | 10.00% | 10.00% |
| Diethylhexyl malate | 0.00% | 9.55% | 0.00% | 0.00% |
| Bodying Agent and Film-Former | | | | |
| Stearyl alcohol | 1.00% | 1.00% | 1.00% | 1.00% |
| $C_{30}$–$C_{38}$ olefin/Isopropyl maleate/MA copolymer | 2.00% | 2.00% | 2.00% | 2.00% |
| Emulsifiers | | | | |
| Steareth 21 | 0.30% | 0.33% | 0.70% | 0.70% |
| Steareth 2 | 0.20% | 0.18% | 0.40% | 0.40% |
| Polyglyceryl-3 methyl glucose distearate | 3.00% | 3.00% | 3.00% | 3.00% |
| Water Phase | | | | |
| Disodium EDTA | 0.05% | 0.05% | 0.05% | 0.05% |
| Glycerin | 3.00% | 3.00% | 3.00% | 3.00% |
| Methylpropanediol | 2.00% | 2.00% | 2.00% | 2.00% |
| Phenoxyethanol & Methylparaben & Ethylparaben & Propylparaben & Butylparaben | 0.60% | 0.60% | 0.60% | 0.60% |
| Stabilizer and Neutralizer | | | | |
| Carbomer | 0.20% | 0.20% | 0.20% | 0.20% |
| Sodium hydroxide (25% solution) | 0.28% | 0.28% | 0.28% | 0.28% |
| Water | 66.37% | 65.36% | 64.77% | 69.77% |
| Rate Constant of Photodecay (k) | 0.009 | 0.017 | 0.070 | 0.436 |

Oil-in-water emulsions were created, wherein the aqueous phase was made up of water, the water phase ingredients, the stabilizer and neutralizer, the emulsifiers, and the bodying agent and film-former listed above. The resulting sunscreens were tested for photostability by measuring absorbance on a Labsphere UV-1000S Ultraviolet Transmittance Analyzer (software version 1.27) before and after irradiation with a Solar Light Company model 16S solar simulator (equipped with a WG 320 filter to transmit radiation greater than 290 nm) in 5 MED increments up to 30 MED. Output was monitored by a PMA 2105 UV-B DCS Detector (biologically weighted) and controlled by a PMA 2100 Automatic Dose Controller (Solar Light Co.).

To test stability, a slide was positioned on the UV transmittance analyzer using registration marks, and a scan of a 1 cm spot on the slide was performed. The slide was then transferred to a holder placed adjacent to the solar simulator and, using a calipers, was positioned such that the beam of UV radiation exiting the solar simulator illuminated the same 1 cm spot on the slide. The following software settings were used: UV-B=290–320 nm; UV-A=320–400 nm. Following an exposure of 5 MED, the slide was again placed in position on the UV transmittance analyzer, and a scan of the exposed spot was performed. The procedure was repeated on the same 1 cm spot on the slide until the desired total radiation dosage was achieved.

The absorbance versus cumulative MED data at 370 nm (approximate peak absorbance for avobenzone) were fit to equation (i), described above, to calculate the rate constant of photodecay for each formulation.

FIG. 1 is a graph of the percent absorbance of the sunscreen compositions listed in Table II at various intervals of exposure to radiation. This figure shows the increase in the absorbance at 370 nm by the addition of very low levels of octocrylene to a composition including avobenzone and 5% by weight of DEHN. Without intending to be limited to a particular mechanism of action, it is believed that in a composition including an α-cyano-β,β-diphenylacrylate compound and a diester or polyester of naphthalene dicarboxylic acid, depending on the relative concentrations of the α-cyano-β,β-diphenylacrylate and the diester or polyester, one of the compounds would exclusively dominate the photostability profile. Thus, one would expect that at high concentration of a diester or polyester of naphthalene dicarboxylic acid compound, the addition of low and very low levels of an α-cyano-β,β-diphenylacrylate compound would not increase the overall photostability of the dibenzoylmethane derivative. It has been found, quite surprisingly however, that at low and very low levels of α-cyano-β,β-diphenylacrylate compound, the combination works synergistically to provide even greater stabilization of a dibenzoylmethane derivative than would be expected. Without intending to be limited to any particular mechanism of operation, it is believed that the relatively high concentration of diester or polyester of naphthalene dicarboxylic acid provides a sufficient amount the diesters or polyesters in proximity to dibenzoylmethane derivatives and, as the dibenzoylmethane derivatives are excited to their triplet excited states, the diester or polyester accepts the triplet excited energy at a sufficient rate to substantially reduce or prevent degradation of the dibenzoylmethane derivative. At the same time, however, the relatively low amount of α-cyano-β,β-diphenylacrylate compound is believed to rapidly accept triplet excited energy from the relatively numerous diester or polyester molecules around it in solution, and very rapidly dissipate the energy through a rapid isomerization mechanism, thus generating ground state diesters or polyesters of naphthalene dicarboxylic acid that are once again able to accept excited state energy from an excited dibenzoylmethane derivative. Thus, the two compounds, in the relative amounts disclosed herein, can operate synergistically to stabilize a dibenzoylmethane derivative more than either compound alone or the expected combination.

In addition, as shown in FIG. 1, a stable composition was formed in a composition including low levels of octocrylene and 5% by weight of DEHN.

Example 2

A series of sunscreen compositions was produced and tested for photostability in the same manner described with reference to Example 1, above. The addition of 0.20% by weight diethylhexyl malate to the control was to maintain identical oil phase volumes in all formulations tested. The sunscreen compositions included very low ratios of octocrylene (OC) to DEHN (diester or polyester of naphthalene dicarboxylic acid) of 0.06 and 0.026, and are shown in Table III:

TABLE III

| Ingredients | 0.45% Octocrylene OC:DEHN 0.06 | 0.20% Octocrylene OC:DEHN 0.026 | 0% Octocrylene Control |
|---|---|---|---|
| Oil Phase | | | |
| Avobenzone | 3.00% | 3.00% | 3.00% |
| Octyl salicylate | 5.00% | 5.00% | 5.00% |
| Diethyihexyl 2,6-naphthalate | 7.50% | 7.75% | 7.75% |
| Octocrylene | 0.45% | 0.20% | 0.00% |
| Homosalate | 5.00% | 5.00% | 5.00% |
| Diethyihexyl malate | 0.00% | 0.00% | 0.20% |
| Benzophenone-3 | 0.49% | 0.49% | 0.49% |
| Bodying Agent and Film-Former | | | |
| Stearyl alcohol | 1.00% | 1.00% | 1.00% |
| $C_{30}$–$C_{38}$ olefin/Isopropyl maleate/MA copolymer | 2.00% | 2.00% | 2.00% |
| Emulsifiers | | | |
| Steareth 21 | 0.31% | 0.31% | 0.31% |
| Steareth 2 | 0.19% | 0.19% | 0.19% |
| Polyglyceryl-3 methyl glucose distearate | 3.00% | 3.00% | 3.00% |
| Water Phase | | | |
| Disodium EDTA | 0.05% | 0.05% | 0.05% |
| Glycerin | 4.00% | 4.00% | 4.00% |
| Methylpropanediol | 2.00% | 2.00% | 2.00% |

TABLE III-continued

| Ingredients | 0.45% Octocrylene OC:DEHN 0.06 | 0.20% Octocrylene OC:DEHN 0.026 | 0% Octocrylene Control |
|---|---|---|---|
| Phenoxyethanol & Methylparaben & Ethylparaben & Propylparaben & Butylparaben Stabilizer and Neutralizer | 0.60% | 0.60% | 0.60% |
| Carbomer | 0.20% | 0.20% | 0.20% |
| Sodium hydroxide (25% solution) | 0.03% | 0.03% | 0.03% |
| Water | 61.62% | 61.62% | 61.62% |

Figure 2:
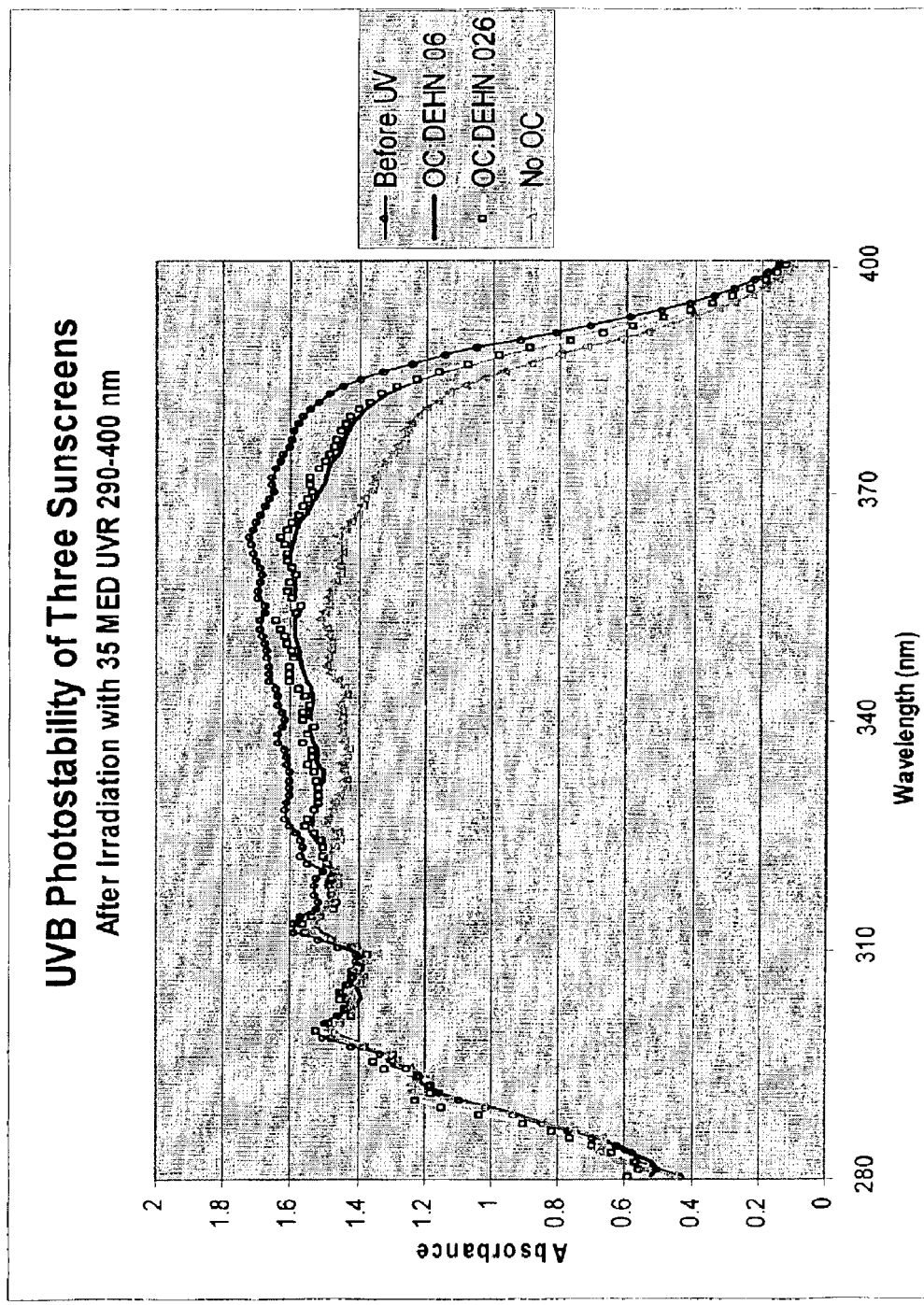
FIG. 2 is a graph of the UVB photostability of three sunscreen compositions of Table III after irradiation with 35 MED radiation.
Figure 3:
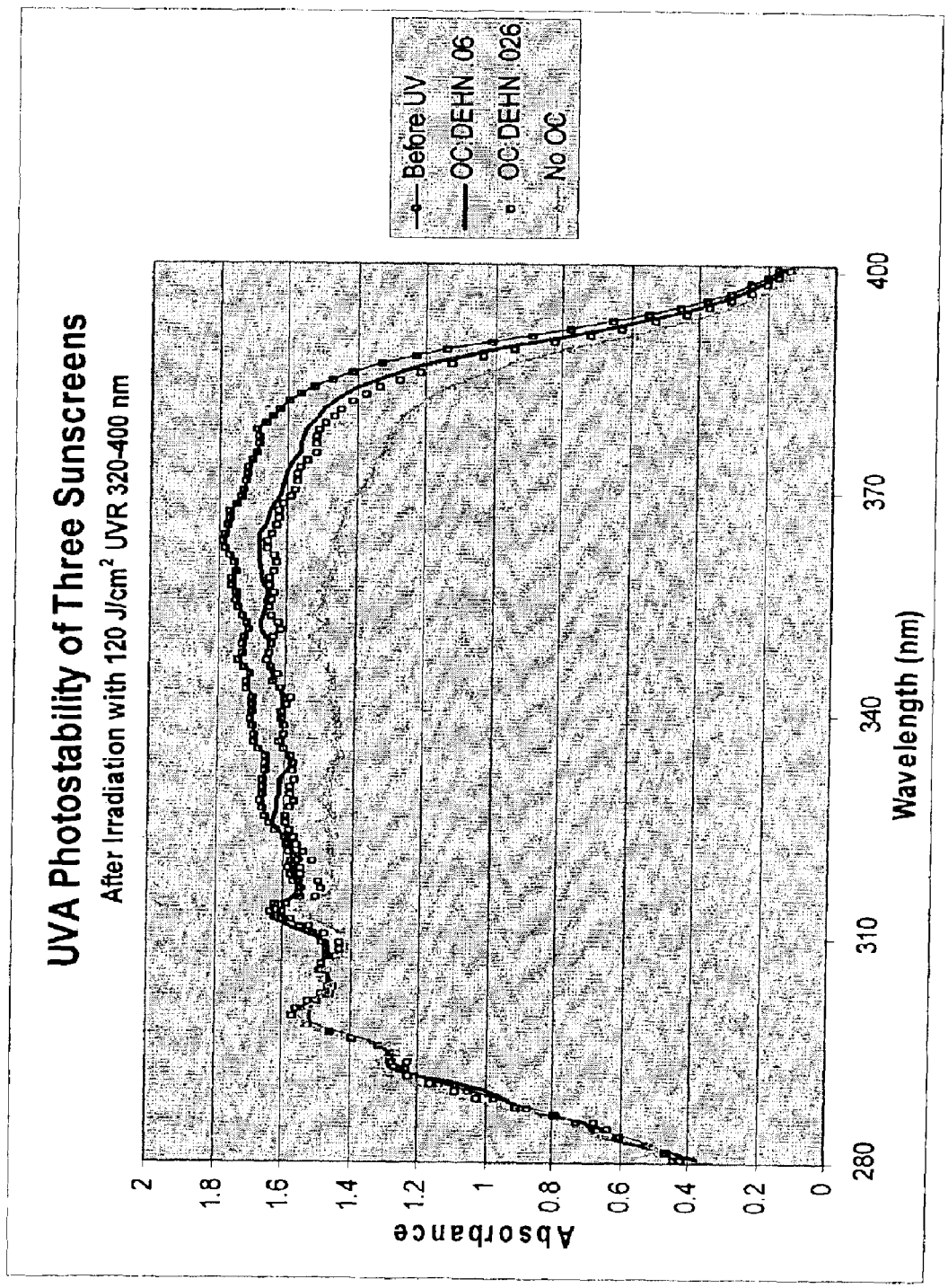
FIG. 3 is a graph of the UVA photostability of three sunscreen compositions of Table III after irradiation with 120 J/cm$^2$ radiation.

FIGS. 2 and 3 are graphs of the percent absorbance of the sunscreen compositions of Table III at various levels of exposure to UVB and UVA radiation, respectively. FIGS. 2 and 3 show that using ultra-low levels of octocrylene (0.20%) to provide a weight ratio of octocrylene (OC) to DEHN of 0.026, the photostability is equivalent to the 0.06 OC to DEHN ratio. Even more surprising, as shown in FIG. 2, the formulation having the OC:DEHN ratio of 0.026 was better than the formulation having an OC:DEHN ratio of 0.06 for maintaining photostability in the UVB range.

Example 3

Another series of sunscreen compositions was produced according to the ingredients and concentrations (formulations) shown in Table IV below:

TABLE IV

| Ingredients | 0.45% Octocrylene, Dielectric Constant and Benzophenone (wt %) | 0.45% Octocrylene and Dielectric Constant (wt %) | 0.45% Octocrylene (wt %) | Dielectric Constant (wt %) | Control (wt %) |
|---|---|---|---|---|---|
| Oil Phase | | | | | |
| Avobenzone | 2.00% | 2.00% | 2.00% | 2.00% | 2.00% |
| Octyl salicylate | 5.00% | 5.00% | 5.00% | 5.00% | 5.00% |
| Homosalate | 5.00% | 5.00% | 5.00% | 5.00% | 5.00% |
| Octocrylene | 0.45% | 0.45% | 0.45% | 0.00% | 0.00% |
| Benzophenone-3 | 0.45% | 0.00% | 0.00% | 0.00% | 0.00% |
| $C_{12}$–$C_{15}$ alkyl benzoates | 0.00% | 0.00% | 10.00% | 0.00% | 10.45% |
| Diethylhexyl malate | 5.00% | 5.00% | 0.00% | 5.00% | 0.00% |
| N,N-dimethyldecanamide Bodying Agent and Film-Former | 5.00% | 5.00% | 0.00% | 5.45% | 0.00% |
| Stearyl alcohol | 1.00% | 1.00% | 1.00% | 1.00% | 1.00% |
| $C_{30}$–$C_{35}$ olefin/Isopropyl maleate/MA copolymer Emulsifiers | 2.00% | 2.00% | 2.00% | 2.00% | 2.00% |
| Steareth 21 | 0.30% | 0.35% | 0.37% | 0.35% | 0.37% |
| Steareth 2 | 0.25% | 0.30% | 0.20% | 0.29% | 0.20% |
| Polyglyceryl-3 methyl glucose distearate | 3.00% | 3.00% | 3.00% | 3.00% | 3.00% |
| Water Phase | | | | | |
| Disodium EDTA | 0.05% | 0.05% | 0.05% | 0.05% | 0.05% |
| Glycerin | 3.00% | 3.00% | 3.00% | 3.00% | 3.00% |
| Methylpropanediol | 2.00% | 2.00% | 2.00% | 2.00% | 2.00% |
| Phenoxyethanol & Methylparaben & Ethylparaben & Propylparaben & Butylparaben Stabilizer and Neutralizer | 0.60% | 0.60% | 0.60% | 0.60% | 0.60% |
| Carbomer | 0.20% | 0.20% | 0.20% | 0.20% | 0.20% |
| Sodium hydroxide (25% solution) | 0.28% | 0.28% | 0.28% | 0.28% | 0.28% |

TABLE IV-continued

| Ingredients | 0.45% Octocrylene, Dielectric Constant and Beuzophenone (wt %) | 0.45% Octocrylene and Dielectric Constant (wt %) | 0.45% Octocrylene (wt %) | Dielectric Constant (wt %) | Control (wt %) |
|---|---|---|---|---|---|
| Water | 64.42% | 64.77% | 64.85% | 64.78% | 64.85% |
| Dielectric Constant of the Oil Phase (ε) | 9.08 | 9.01 | 5.70 | 9.10 | 5.55 |
| Rate Constant of Photodecay (k) | 0.0555 | 0.0738 | 0.1563 | 0.1761 | 0.4143 |

For each sunscreen composition, the photoactive compounds were blended with the components listed above to form an oil phase. Next, the dielectric constant of the oil phase was measured. Dielectric constant measurements were performed with a Scientifica model 850 dielectric constant meter.

Oil-in-water emulsions were created, wherein the aqueous phase was made up of water, the water phase ingredients, the stabilizer and neutralizer, the emulsifiers, and the bodying agent and film-former listed above. The resulting sunscreens were tested for photostability by measuring absorbance on a Labsphere UV-1000S Ultraviolet Transmittance Analyzer (software version 1.27) before and after irradiation with a Solar Light Company model 16S solar simulator (equipped with a WG 320 filter to transmit radiation greater than 290 nm) in 5 MED increments up to 30 MED. Output was monitored by a PMA 2105 UV-B DCS Detector (biologically weighted) and controlled by a PMA 2100 Automatic Dose Controller (Solar Light Co.).

To test stability, a slide was positioned on the UV transmittance analyzer using registration marks, and a scan of a 1 cm spot on the slide was performed. The slide was then transferred to a holder placed adjacent to the solar simulator and, using a calipers, was positioned such that the beam of UV radiation exiting the solar simulator illuminated the same 1 cm spot on the slide. The following software settings were used: UV-B=290–320 nm; UV-A=320–400 nm. Following an exposure of 5 MED, the slide was again placed in position on the UV transmittance analyzer, and a scan of the exposed spot was performed. The procedure was repeated on the same 1 cm spot on the slide until the desired total radiation dosage was achieved.

The absorbance versus cumulative MED data at 370 nm (approximate peak absorbance for avobenzone) were fit to equation (i), described above, to calculate the rate constant of photodecay for each formulation.

Figure 4:
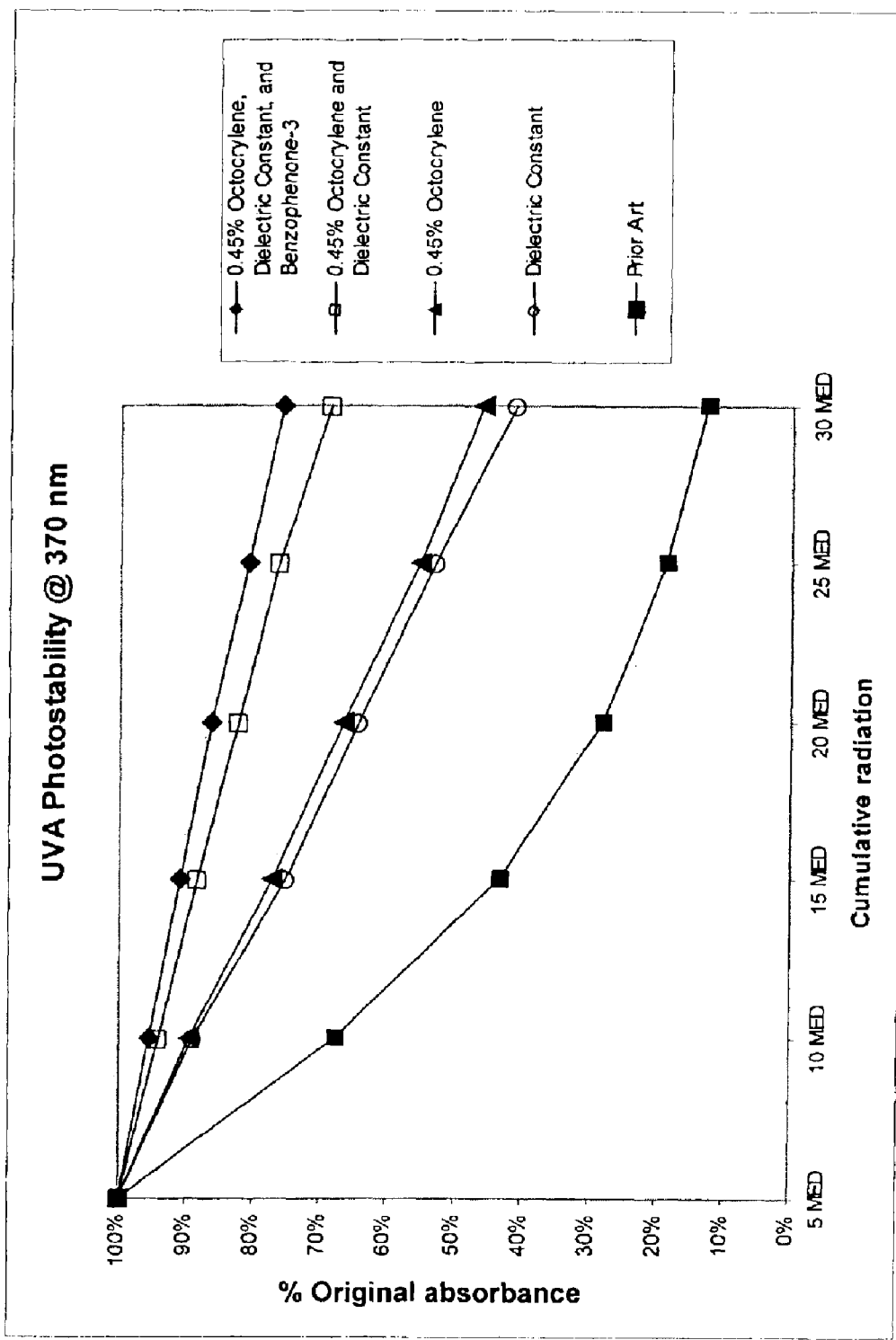
FIG. 4 is a graph of the percent absorbance of the sunscreen compositions listed in Table IV at various intervals of exposure to radiation in MED units.

FIG. 4 is a graph of the percent absorbance of the sunscreen compositions listed in Table IV at various intervals of exposure to radiation.

What is claimed is:

1. A sunscreen composition, comprising a mixture of (a) from about 0.1% to about 25% by weight of the total weight of the composition of a dibenzoylmethane derivative, (b) less than 1% by weight of the total weight of the composition of an α-cyano-β,β-diphenylacrylate compound, (c) a diester or polyester of naphthalene dicarboxylic acid selected from the group consisting of formula (I), formula (II), and combinations thereof:

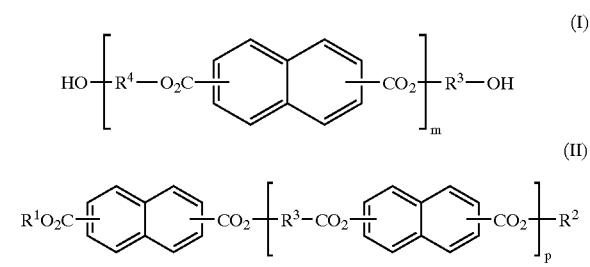

wherein $R^1$ and $R^2$ are the same or different and selected from the group consisting of $C_1$–$C_{22}$ alkyl groups, diols having the structure HO—$R^3$—OH, and polyglycols having the structure HO—$R^4$—(—O—$R^3$—)$_n$—OH; wherein each $R^3$ and $R^4$ is the same or different and selected from the group consisting of $C_1$–$C_6$ straight or branched chain alkyl groups; wherein m and n are each in a range of 1 to 100 and p is in a range of 0 to 100; and (d) benzophenone-3 is present in an amount of 0.5% or less by weight of the total weight of the composition, wherein said amount is sufficient to increase the photostability of the dibenzoylmethane derivative, and wherein the weight ratio of (b) to (c) is 0.01 to 0.027.

2. The composition of claim 1, wherein the weight ratio of (b) to (c) is 0.01 to 0.026.

3. The composition of claim 1, wherein said dibenzoylmethane derivative is selected from the group consisting of 2-methyldibenzoylmethane; 4-methyldibenzoylmethane; 4-isopropyldibenzoylmethane; 4-tert-butyldibenzoylmethane; 2,4-dimethyldibenzoylmethane; 2,5-dimethyldibenzoylmethane; 4,4'-diisopropyldibenzoylmethane; 4,4'-dimethoxydibenzoylmethane; 4-tert-butyl-4'-methoxydibenzoylmethane; 2-methyl-5-isopropyl-4'-methoxydibenzoylmethane; 2-methyl-5-tert-butyl-4'-methoxydibenzoylmethane; 2,4-dimethyl-4'-methoxydibenzoylmethane; 2,6-dimethyl-4'-tert-butyl-4'-methoxydibenzoylmethane, and combinations thereof.

4. The composition of claim 1, wherein said α-cyano-β,β-diphenylacrylate compound is present in an amount of at least about 0.1% by weight of the total weight of the composition.

5. The composition of claim 4, wherein said α-cyano-β,β-diphenylacrylate compound is present in an amount less than 0.5% by weight of the total weight of the composition.

6. The composition of claim 5, wherein said α-cyano-β,β-diphenylacrylate compound is present in a range of 0.1% to 0.45% by weight of the total weight of the composition.

7. The composition of claim 6, wherein said α-cyano-β,β-diphenylacrylate compound comprises 2-ethylhexyl-2-cyano-3,3-diphenylacrylate.

8. The composition of claim 1, comprising a diester of formula (II) wherein $R^1$ and $R^2$ are 2-ethylhexane and p is 0.

9. The composition of claim 1, wherein said diester or polyester of naphthalene dicarboxylic acid is present in a range of about 0.1% to about 15% by weight of the total weight of the composition.

10. The composition of claim 1, wherein the weight ratio of (b) to (c) is less than 0.03.

11. The composition of claim 1, further comprising a photoactive compound selected from the group consisting of p-aminobenzoic acid and salts and derivatives thereof; anthranilate and derivatives thereof; dibenzoylmethane and derivatives thereof; salicylate and derivatives thereof; cinnamic acid and derivatives thereof; dihydroxycinnamic acid and derivatives thereof; camphor and salts and derivatives thereof; trihydroxycinnamic acid and derivatives thereof; dibenzalacetone naphtholsulfonate and salts and derivatives thereof; benzalacetophenone naphtholsulfonate and salts thereof; dihydroxy-naphthoic acid and salts thereof; o-hydroxydiphenyldisulfonate and salts thereof; p-hydroxydiphenyldisulfonate and salts thereof; coumarin and derivatives thereof; diazole derivatives; quinine and salts thereof; quinoline derivatives; hydroxy-substituted benzophenone derivatives; methoxy-substituted benzophenone derivatives; tannic acid; hydroquinone; benzophenone derivatives; 1,3,5-triazine derivatives, phenyldibenzimidazole tetrasulfonate and salts and derivatives thereof; terephthalylidene dicamphor sulfonic acid and salts and derivatives thereof; methylene bis-benzotriazolyl tetramethylbutylphenol and salts and derivatives thereof; bis-ethylhexyloxyphenol methoxyphenyl triazine and salts and derivatives thereof; diethylamino hydroxybenzoyl hexyl benzoate and salts and derivatives thereof; and combinations of the foregoing.

12. The composition of claim 11, wherein said photoactive compound comprises 2-ethylhexyl-p-methoxycinnamate.

13. The composition of claim 1, comprising an oil phase comprising said dibenzoylmethane derivative, said α-cyano-β,β-diphenylacrylate compound, said diester or polyester of naphthalene dicarboxylic acid, and a solvent system, wherein said solvent system comprises an effective amount of a polar solvent to increase the photostability of said dibenzoylmethane derivative and to increase the dielectric constant of the oil phase to at least about 7.

14. The composition of claim 13, wherein said oil phase has a dielectric constant of at least about 8.

* * * * *